US012611144B2

(12) United States Patent
Richter et al.

(10) Patent No.: US 12,611,144 B2
(45) Date of Patent: Apr. 28, 2026

(54) IMPLANT

(71) Applicant: Fraunhofer-Gesellschaft zur Förderung der angewandten Forschung e.V., Munich (DE)

(72) Inventors: Martin Richter, Munich (DE); Lorenz Grünerbel, Munich (DE); Sebastian Kibler, Munich (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 836 days.

(21) Appl. No.: 17/938,094

(22) Filed: Oct. 5, 2022

(65) Prior Publication Data

US 2023/0029038 A1    Jan. 26, 2023

Related U.S. Application Data

(63) Continuation of application No. PCT/EP2020/060074, filed on Apr. 8, 2020.

(51) Int. Cl.
*A61B 5/00* (2006.01)
*A61B 5/03* (2006.01)
*G01L 7/08* (2006.01)

(52) U.S. Cl.
CPC .............. *A61B 5/6885* (2013.01); *A61B 5/03* (2013.01); *G01L 7/08* (2013.01)

(58) Field of Classification Search
CPC ..... A61B 5/6885; A61B 5/03; A61B 2562/04; A61B 5/205; A61B 5/01;

(Continued)

(56) References Cited

U.S. PATENT DOCUMENTS 4,460,568 A    7/1984 Strasilla
4,571,749 A *    2/1986 Fischell ................. A61F 2/004
600/561

(Continued)

FOREIGN PATENT DOCUMENTS

CN        102711593 A    10/2012
CN        110520031 A    11/2019

(Continued)

OTHER PUBLICATIONS

Japanese language office action dated Jan. 9, 2024, issued in application No. JP 2022-561406.

(Continued)

*Primary Examiner* — May A Abouelela
(74) *Attorney, Agent, or Firm* — McClure, Qualey & Rodack, LLP

(57) ABSTRACT

An implant which includes: a housing having a chamber; and a sensor unit; a first membrane covering the chamber at a first pressure side and a second membrane covering the chamber at a second pressure side; the chamber includes a pressure transfer device being in contact to the first and second membrane and to the sensor unit arranged within the chamber between the first and second membrane, wherein a sensor control unit arranged within the housing; wherein the sensor unit is configured to determine a pressure difference between a pressure at the first pressure side of the chamber and a pressure at the second pressure side chamber of the chamber.

13 Claims, 12 Drawing Sheets

(58) Field of Classification Search

CPC ...... A61B 2562/0247; A61B 2562/168; A61B 5/686; G01L 7/08; A61F 2/004; A61F 2002/045; A61F 2002/044

See application file for complete search history.

(56) References Cited

U.S. PATENT DOCUMENTS

| | | | | |
|---|---|---|---|---|
| 4,660,568 | A | 4/1987 | Cosman | |
| 6,939,299 | B1* | 9/2005 | Petersen | A61B 3/16 600/587 |
| 7,096,737 | B2* | 8/2006 | Coleman | G01L 9/0039 73/715 |
| 7,434,471 | B2* | 10/2008 | Lukens | G01L 19/06 73/726 |
| 9,333,071 | B2* | 5/2016 | Boyden | A61F 2/12 |
| 10,258,240 | B1* | 4/2019 | Eberle | A61B 5/0084 |
| 10,258,284 | B1 | 4/2019 | Malek | |
| 10,517,525 | B2* | 12/2019 | Yoon | A61B 5/681 |
| 10,612,990 | B2* | 4/2020 | Klehr | G01L 19/0627 |
| 10,736,571 | B1* | 8/2020 | Peyman | A61B 5/4041 |
| 10,983,023 | B2* | 4/2021 | Ens | G01L 19/0618 |
| 11,819,277 | B2* | 11/2023 | Sherwood | A61B 5/686 |
| 2002/0020221 | A1* | 2/2002 | Sittler | G01L 9/0075 73/715 |
| 2002/0045921 | A1* | 4/2002 | Wolinsky | A61N 1/3787 607/61 |
| 2004/0019285 | A1* | 1/2004 | Eigler | A61B 5/4884 600/488 |
| 2006/0211913 | A1* | 9/2006 | Dlugos | A61F 5/0003 600/37 |
| 2006/0272422 | A1* | 12/2006 | Yoneda | G01L 19/0618 73/724 |
| 2013/0233086 | A1* | 9/2013 | Besling | G01L 13/026 29/825 |
| 2014/0206976 | A1* | 7/2014 | Thompson | A61B 5/25 600/391 |
| 2015/0382116 | A1* | 12/2015 | Van Gerwen | H04R 25/00 600/25 |
| 2017/0172505 | A1* | 6/2017 | Ruben | H05K 5/069 |
| 2017/0281092 | A1* | 10/2017 | Burnette | A61B 5/7225 |
| 2018/0164221 | A1* | 6/2018 | Singh | A61K 49/0058 |
| 2018/0263688 | A1* | 9/2018 | Barrish | A61B 5/6853 |
| 2019/0054304 | A1* | 2/2019 | Maile | A61N 1/3756 |
| 2019/0175015 | A1* | 6/2019 | Adams | A61B 5/6861 |
| 2019/0343388 | A1* | 11/2019 | Bahmanyar | A61B 5/036 |
| 2019/0343425 | A1* | 11/2019 | Jones | A61B 5/07 |
| 2019/0365249 | A1* | 12/2019 | Verkaik | A61B 5/0225 |
| 2020/0214684 | A1* | 7/2020 | Mcauliffe | A61F 2/4657 |
| 2020/0261200 | A1* | 8/2020 | Cook | A61F 2/004 |
| 2020/0305741 | A1* | 10/2020 | Gunn | A61B 5/6821 |
| 2021/0100513 | A1* | 4/2021 | Bahmanyar | A61B 5/0215 |
| 2021/0127998 | A1* | 5/2021 | Nguyen | A61L 31/148 |
| 2021/0145335 | A1* | 5/2021 | Shtein | A61K 9/0009 |
| 2021/0244305 | A1* | 8/2021 | Gleich | A61M 25/0127 |
| 2022/0176088 | A1* | 6/2022 | Salahieh | A61B 5/686 |

FOREIGN PATENT DOCUMENTS

| | | |
|---|---|---|
| DE | 102010031659 A1 | 1/2012 |
| JP | 2013-181951 A | 9/2013 |
| JP | 2015-111055 A | 6/2015 |
| JP | 2019-518546 A | 7/2019 |

OTHER PUBLICATIONS

English language counterpart to office action dated Jan. 9, 2024 (pp. 3-5).

Korean language office action dated May 24, 2024, issued in application No. KR 10-2022-7039185.

Chinese language office action dated May 8, 2025, issued in application No. CN 202080100489.3 (English language translation, pp. 1-8 of attachment).

Anonymous, "Capacitance Differential Pressure Transmitter Working Principle - Eastsensor Technology", (Apr. 9, 2018), URL: https://www.eastsensor.com/blog/capacitance-differential-pressure-transmitter-working-principle/, (Dec. 8, 2020), XP055758132.

Aubrey Shapero; Yu-Chong Tai, Parylene-oil-encapsulated low-drift implantable pressure sensors. MEMS 2018, Belfast, Northern Ireland, UK, Jan. 21-25, 2018.

Implantable absolute pressure sensor e.g. HELGA from Fraunhofer IDMT / New intracranial sensor serves to measure cerebral pressure, PHYSORG Nov. 1, 2012.

International Search Report and Written Opinion issued in international application No. PCT/EP2020/060074, dated Dec. 17, 2020.

* cited by examiner

IMPLANT

CROSS-REFERENCES TO RELATED APPLICATIONS

This application is a continuation of copending International Application No. PCT/EP2020/060074, filed Apr. 8, 2020, which is incorporated herein by reference in its entirety.

BACKGROUND OF THE INVENTION

Embodiments of the present invention refer to an implant having a differential pressure sensor and to a method for manufacturing same. In general embodiments refer to a concept of pressure difference measurement in the body.

A plurality of applications for pressure measurement within a human body or a body are available. Examples are Pressure difference measurement of the eye with respect to body liquid Pressure difference measurement of the cuff reservoir pressure of sphincter to the cuff Pressure difference measurement of the vessel blood reservoir pressure or the heart pressure to the body pressure However, the body pressure is not constant. If the pressure of the environment is changing, the pressure of the body is following the atmosphere pressure. Reasons for this are:

Changes of the pressure due to normal changes of the atmosphere pressure at a given location Changes of the pressure due to height (e.g. mountain hiking)

Changes of the pressure inside an airplane

These changes of the atmosphere pressure are in the same order of magnitude or even higher than the pressure difference measurement.

The prior art which will be discussed with respect to FIG. 1a to FIG. 1c show pressure sensors. FIG. 1a an implantable absolute pressure sensor, e.g., the pressure sensor called HELGA. The pressure sensor is embedded in a liquid, which is inside a hermetic sealed titanium housing. The thin titanium foil will transfer the pressure from the body to the liquid and the sensor.

However, this is just an absolute pressure sensor, so pressure changes caused by the environment lead to the situation, that the pressure value could not be used correctly. Background is that for some applications, the pressure difference between e.g. an implant and the surrounding body liquid is essential. Hence, if the body liquid pressure varies due to environmental conditions, the implant pressure needs to change as well. The absolute pressure value is not useful.

FIG. 1b shows a sensor similar to the HELG sensor, wherein the sensor is embedded in an oil. This sensor suffers with regard to the same drawbacks.

Within U.S. Pat. No. 4,460,568 a differential implantable pressure sensor is shown. FIG. 1 of this patent is illustrated by FIG. 1c. This pressure sensor uses two diaphragms. However, there is a fixed connection between the pressure sensor and the diaphragms. This can cause the problem of large stress and drift to the pressure sensor. FIG. 1d shows a differential pressure sensor (cf.www.eastsensor.com/blog/capacitance-differential-pressure-transmitter-working-principle/).

SUMMARY

An embodiment may have an implant having: a housing with a chamber; a sensor unit; a first membrane covering the chamber at a first pressure side and a second membrane covering the chamber at a second pressure side; wherein the chamber comprises a pressure transfer device being in contact to the first and second membrane and to the sensor unit arranged within the chamber between the first and second membrane; wherein a sensor control unit arranged within the housing; wherein the sensor unit is configured to determine a pressure difference between a pressure at the first pressure side of the chamber and a pressure at the second pressure side chamber of the chamber; wherein the chamber extends from the first pressure side to the second pressure side through the housing and wherein the housing comprises a diaphragm separating the chamber in a first and a second part; wherein the diaphragm holds the sensor unit; wherein the first membrane comprises a first foil and wherein the second membrane comprises a second foil and wherein the chamber is covered by the first foil on the first pressure side and by the second foil on the second pressure side so as to hermetically seal the chamber; and wherein the implant comprises a fixture to be connected to a body membrane separating two different pressure sides, wherein the sensor unit determines the pressure difference between the two different pressure sides.

Another embodiment may have a cuff reservoir having the implant according to the invention, wherein the is implemented the implant is part of a cuff reservoir, wherein the sensor unit determines the pressure difference between the two different pressures within the cuff reservoir or of the cuff reservoir against the surrounding.

Another embodiment may have a method for producing an implant according to the invention, wherein the method comprises arranging the sensor unit within the chamber and/or between two foils.

Embodiments of the present invention provide an implant which comprises a housing and a sensor unit. It further comprises a first membrane covering the chamber at a first pressure side and a second membrane covering the chamber at a second pressure side (e.g. for hermetically sealing the implant against the surrounding of the implant). The chamber comprises a pressure transfer means (or device) being in contact to the first and second membrane and to the sensor unit arranged within the chamber between the first and second membrane. Further, a sensor control unit is arranged within the housing. The sensor unit is configured to determine a pressure difference between a pressure at the first pressure side of the chamber and a pressure at the second pressure side chamber of the chamber.

According to embodiments, the sensor unit comprises a membrane configured to measure relative pressure between a pressure applied from the first pressure side to a first side of the membrane and a pressure applied from the second pressure side to a second side of the membrane. This embodiment enables beneficially to directly measure the relative/differential pressure. According to another embodiment, the sensor control unit can comprise a first and a second pressure sensor, wherein the first pressure sensor is configured to measure a pressure at the first pressure side and wherein the second pressure sensor is configured to measure a pressure at the second pressure side. Here, the differential pressure is determined starting from the two absolute pressures, wherein the calculation of the differential pressure is performed by the sensor unit.

Embodiments of the present invention are based on the principle that an implant using a housing having a chamber, e.g. formed by a kind of hole/opening within the housing, enables to arrange the sensor unit within the chamber, so that a first pressure from a first pressure side and a second pressure from a second pressure side can be applied to the sensor. This enables to separate locally the task of the hermetic sealing (by the membranes) from the task of a low stress packaging of the pressure difference measuring senor unit (arranged within the pressure transfer means). For example, the chamber can extend from the first pressure side to the second pressure side through the housing. By use of this arrangement, the pressure sensor can directly determine a differential pressure between two sides.

According to embodiments, the housing can comprise a diaphragm enabling to arrange the sensor unit and/or the sensor control unit on this. For example, the diaphragm may be arranged within the chamber. Here, the diaphragm may, according to embodiments, separate the chamber into a first and a second part, wherein then the sensor unit can be attached to the diaphragm and arranged in the middle of the chamber.

According to further embodiments, a first foil as first membrane for the first pressure side or a second foil as second membrane for the second pressure side can be used. Here the housing comprises the first and the second foil. These foils can be arranged such that the sensor unit is arranged between. According to embodiments, the first foil covers the chamber on the first pressure side, wherein the second foil covers the chamber on the second pressure side. According to embodiments, the first foil on the first pressure side and the second foil on the second pressure side hermetically seals the chamber (i.e., the sensor unit arranged within the chamber). According to further embodiments, also, the sensor control unit can be hermetically sealed within the housing, e.g., by use of the first and the second foil. According to embodiments, the pressure of the first pressure side is applied via the first foil to the pressure sensor, wherein the pressure at the second pressure side applied via the second foil to the pressure sensor. In detail, the pressure at the first pressure side may be applied to a first side of the pressure sensor via the first foil, while the pressure at the second pressure side may be applied to a second side of the pressure sensor via the second foil. The first and the second foil enables beneficially to be connected to the housing and hermetically sealing the housing, wherein the sensor unit not in contact to the first and the second foil, thus not influenced during the manufacturing process. However, the foil enables to "forward" the pressure at the different sides. According to embodiments, the first and the second foil may be formed by a titanium foil, a thin titanium foil, or a PEEK foil (Poly Ether Ether Keton).

The chamber, e.g., the chamber closed by the first and the second foil may be filled with an air, an oil, a liquid, or a casting compound as pressure transfer medium. Oil or liquid, advantageously non-conductive, biocompatible and non-corrosive liquid or casting compound are incompressible enabling to apply the pressure from the foil to the sensor in an optimal manner. According to embodiments, the chamber and/or the first and the second foil may comprise a guidance for guiding the liquid, oil or casting mold when being primed.

According to a further embodiment, the housing may comprise a filter, grid, a grid comprising a filter, rigid grid or porous element. Said element surrounds the chamber, e.g., at the first and the second pressure side and/or surrounds the sensor unit from the two pressure sides and/or surrounding the first and the second foil of the housing. This rigid grid enables beneficially to avoid an encapsulation of the foils or the chamber or the sensor unit with body material.

Another embodiment provides a method for producing the implant as discussed above. Here, the method comprises the step of arranging the sensor unit within the chamber, e.g., between the two foils. According to an embodiment, the method may further comprise the step of priming the chamber and/or the area between the two foils. Here, the priming may be performed before or after attaching the foils (first and second foils) to the housing.

BRIEF DESCRIPTION OF THE DRAWINGS

Embodiments of the present invention will be detailed subsequently referring to the appended drawings, in which.

DETAILED DESCRIPTION OF THE INVENTION

Figure 1A:
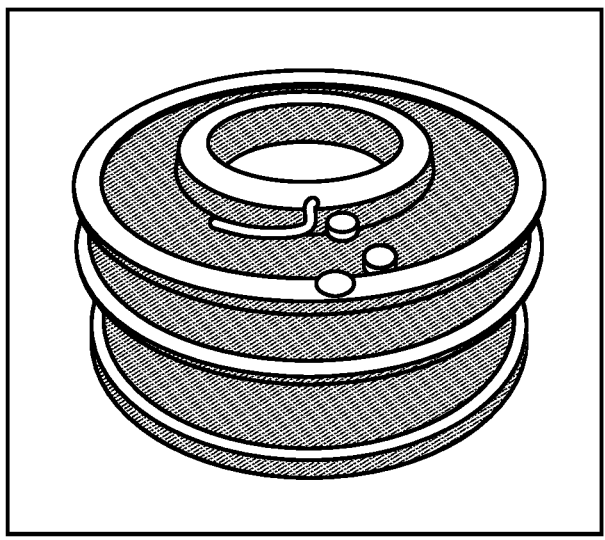
FIGS. 1*a*-1*d* schematically show prior art solutions for implants.
Figure 1B:
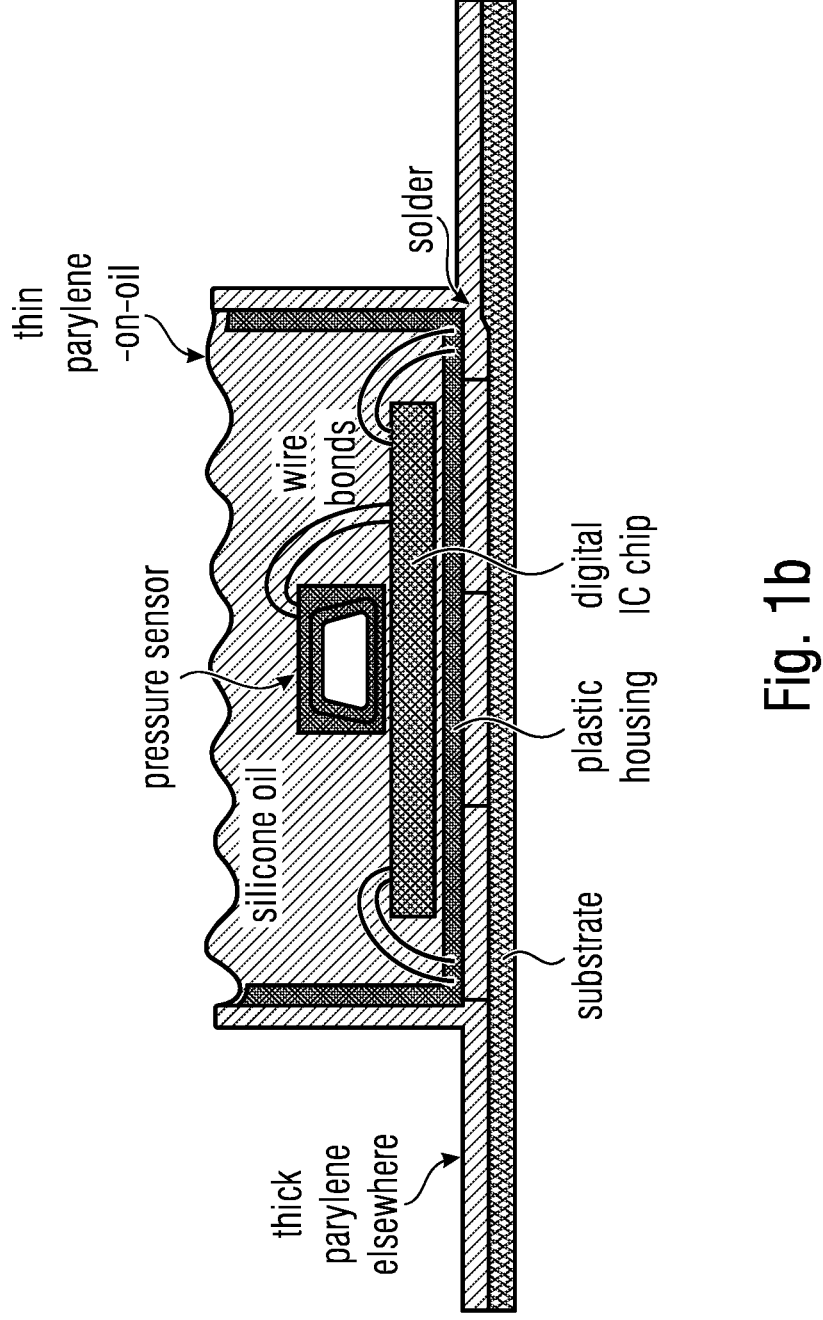
Figure 1C:
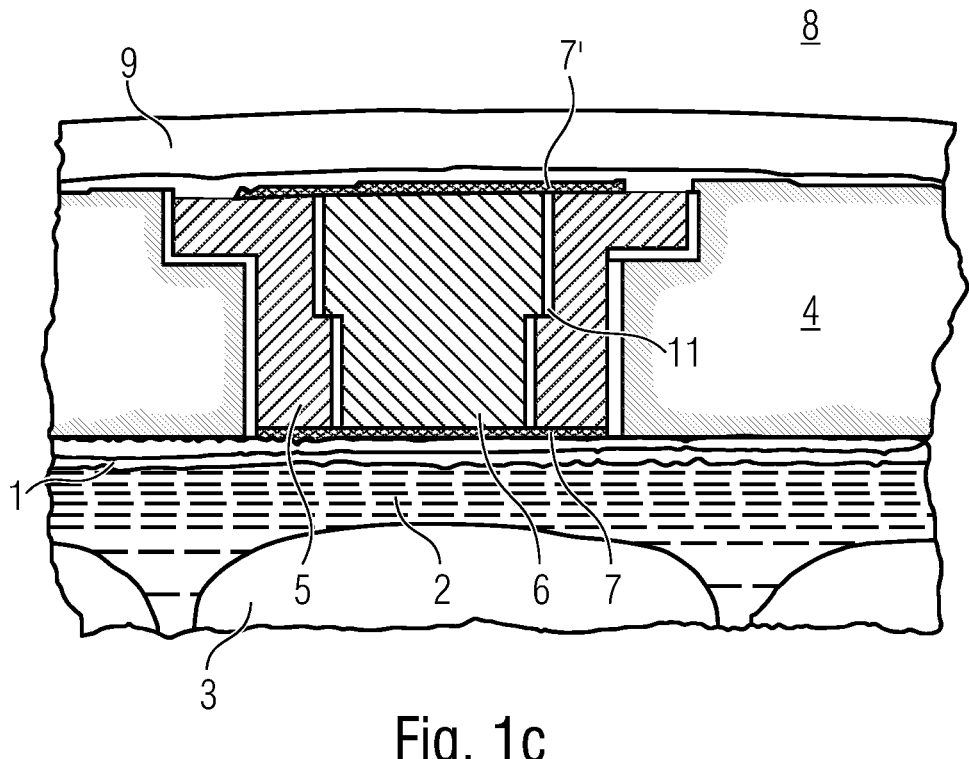
Figure 1D:
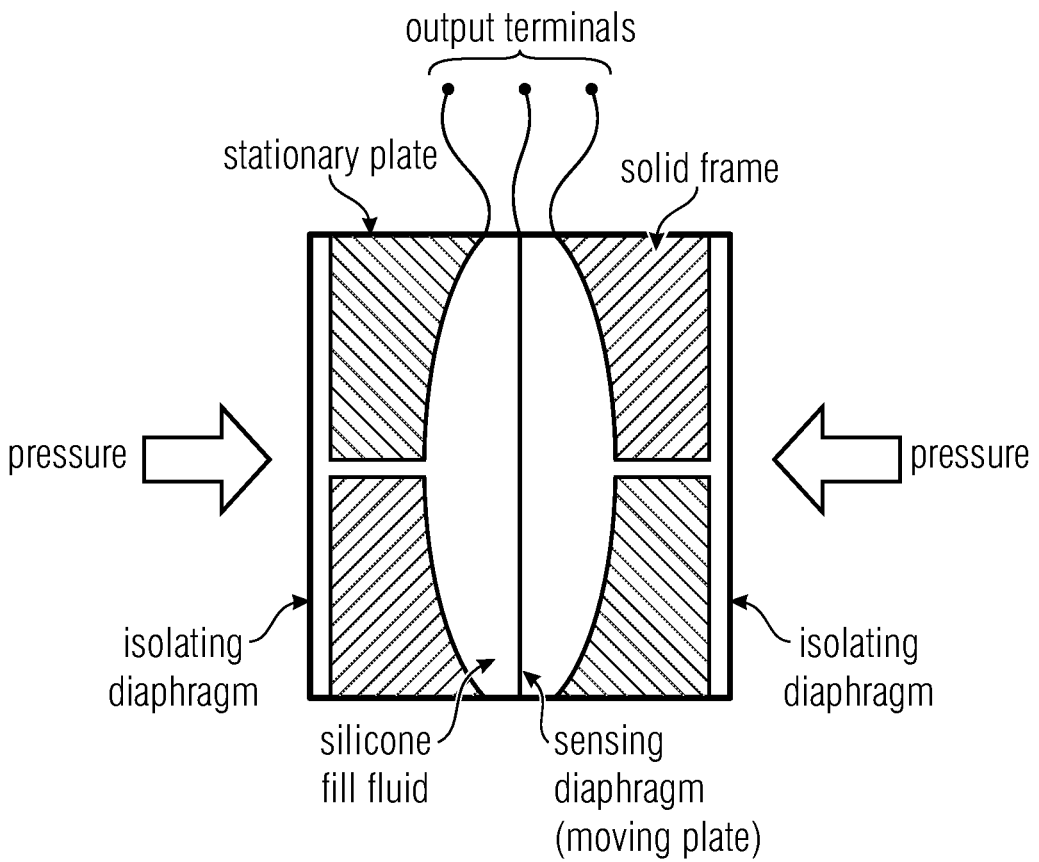

Below, embodiments of the present invention will subsequently be discussed referring to the enclosed figures, wherein identical reference numerals are provided for elements or structures having identical or similar function, so that the description thereof is mutually applicable and interchangeable.

Figure 2:
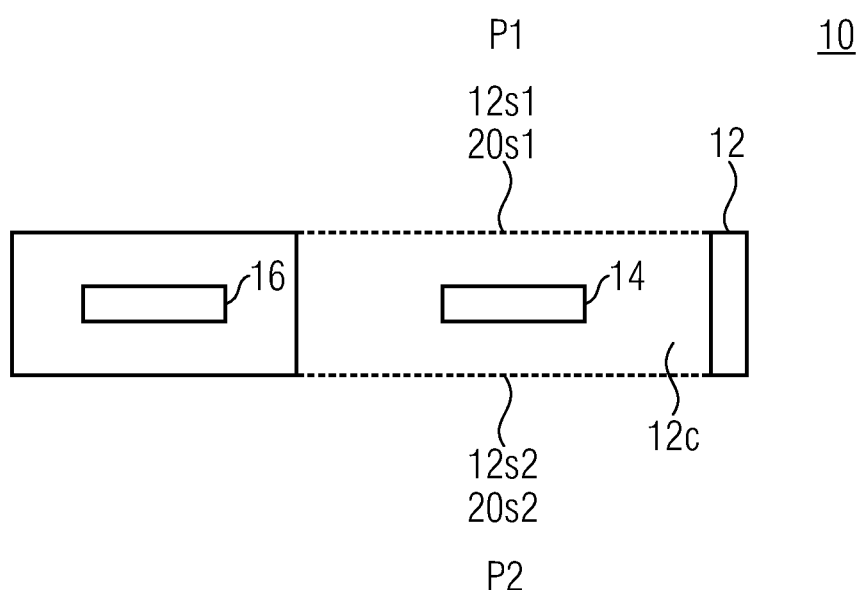
FIG. 2 schematically shows a basic implementation of an implant according to a first embodiment.

FIG. 2 shows an implant 10 comprising a housing 12 which comprises a chamber 12*c*. Within the chamber, a sensor unit 14 may be arranged. Somewhere in the housing 12 a sensor control unit 16 may be arranged.

The chamber 14*c* may be formed, e.g., by a hole extending from a first side of the housing 12 to a second side of the housing 12. Both sides are marked by 12*s*1 and 12*s*2. Via the side 12*s*1, a first pressure P1 can be applied to the sensor 14, wherein a second pressure P2 can be applied to the sensor 14. Since the two pressure levels P1 and P2 are applied from the two sides 12*s*1 and 12*s*2, the two sides 12*s*1 and 12*s*2 are also referred to as first and second pressure side.

According to embodiments, the pressure sensor 14 may be a membrane to which the two pressures P1 and P2 impinge from the two pressure sides 12*s*1 and 12*s*2. Here, the pressure P1 impinges to a first side of the membrane, wherein the pressure P2 impinges to a second side of the membrane. The membrane is moved in accordance to the pressure difference between P1 and P2, wherein this movement can be determined in a piezo-electrical or -resistive manner (advantageous) or capacitive manner. For example, a piezoresistive (differential) pressure sensor uses strain gauges in combination with a membrane to determine the deflection of the membrane and, thus, applied pressure. A piezoelectrical uses a certain material, like a quartz, for the membrane enabling to directly measure the strain to the membrane and, thus, the pressure. Alternatively, the membrane may form a first electrode, wherein a second electrode can be formed by a grid arranged in parallel to the membrane. This arrangement forms a (differential) pressure sensor. According to an alternative variant, the sensor using 14 can be formed by two independent pressure sensors, wherein each pressure sensor determines one of the two pressures P1 and P2, so that the differential pressure between P1 and P2 can be calculated, e.g., by use of the sensor control unit 16. Between the membranes 20$s1$/20$s2$ and the sensor unit 14 a so called pressure transfer medium/means, like a fluid or oil are arranged so as to transfer the pressure p1/p2 from the first and second pressure side 12$s1$/12$s2$, respectively, to the sensor 14. For this the sensor unit 14 may be embedded in the pressure transfer means.

According to embodiments, the chamber 12 may be covered by respective foils (membranes). For example, a first foil 20$s1$ may be applied to the first side 12$s1$ of the chamber 12, wherein a second foil 20$s2$ may be applied to a second side 12$s2$. These two foils 20$s1$ and 20$s2$ covering the chamber 12 from the two sides 12$s1$ and 12$s2$, e.g., so as to hermetically seal same and the elements arranged inside the chamber 12$c$. In detail, the pressure sensor 14 may be arranged between the two foils 20$s1$ and 20$s2$. Here, the two foils 20$s1$ and 20$s2$ may be configured to "forward" the pressure P1 and P2 to the sensor 14.

With respect to the further figures, further optional features according to embodiments will be discussed.

Before discussing the further embodiments and the benefits, especially for the different applications, the field of the applications will be discussed. Preferably the pressure measurement device can be used for measuring a pressure within a human body:

The human body is a system with many different pressure regions (brain, eye, inner ear, colon) and a system where flow is occurring according to pressure differences. These pressure differences are partly huge (like body pressure), partly very small. The only technology which is available is to measure two absolute pressures and subtract these from each other. As body pressure is fluctuating with atmosphere pressure, also these measured pressures are fluctuating with atmosphere pressure. With that it is very difficult to measure those small pressure differences in the body.

A lot of information would be provided about body function, if there would be a technology to measure real pressure differences between two locations in the body.

For that, not an absolute pressure sensor is needed, but a pressure difference sensor, which can measure pressure differences between two locations, which are separated by a body diaphragm.

To measure difference pressure, the pressure sensor has to have contact to both pressure regions to be measured. Next, the pressure sensor has to be electrically contacted, and with it an electrical connection to the system control of an implant. These electrical contacts have to be hermetically sealed. However, pressure sensors are very sensitive to stress. A hermetic sealing, e.g. a hermetic tight bond to a titanium housing, is generating a high stress impact.

For that, it is nearly impossible to bond a pressure sensor chip, which has a pressure contact to two pressure regions, hermetically tight to an implant without inducing a large stress to the pressure sensor.

Figure 3A:
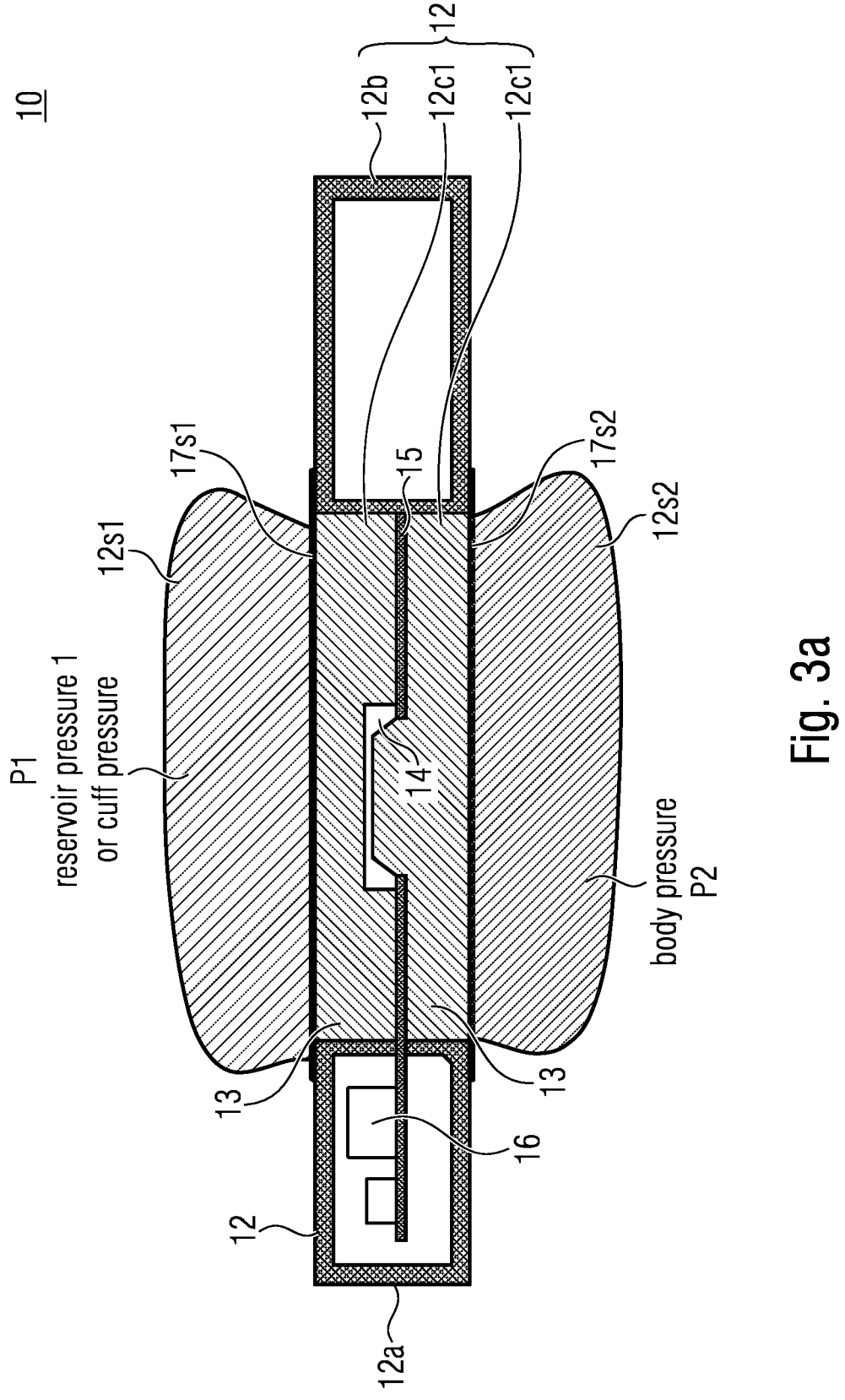
FIGS. 3*a* and 3*b* schematically show an enhanced implementation of an implant, wherein two different sensor units are used according to embodiments.

However, as discussed above, the improved design of the implant, a housing of which comprises a chamber this problem can be solved. Background thereof is that the pressure sensor/differential pressure sensor can be arranged within a chamber so as to be hermetically sealed, e.g., by use of a foil which, vise versa is configured to provide the external pressure to the internal sensor unit. Such a foil can be applied in a stress-less manner. An embodiment comprising such a foil, here a thin titanium foil will be discussed with respect to FIG. 3$a$ and FIG. 3$b$. Both embodiments, FIG. 3$a$ and FIG. 3$b$, are comparable to each other, wherein the used sensor unit is different.

FIG. 3$a$ shows an implant 10 having a housing 12 comprising two portions 12$a$ and 12$b$ (on the first and on the second side with respect to a chamber 12$c$). Within the chamber 12$c$, the differential pressure sensor 14 is arranged. In this embodiment, the pressure sensor 14 is attached to a diaphragm 15 enabling pressure separation (e.g., non-hermetic). The diaphragm 15 extends along a longitudinal direction of the implant 10/housing 12 so as to separate that chamber 12$c$ into a first portion 12$c1$ and a second portion 12$c2$. The first chamber 12$c1$ is arranged at the side 12$s1$, wherein the second chamber 12$c2$ is arranged at the second side 12$s2$. Regarding the diaphragm, it should be noted that this enables to separate the chamber 12$c$ into an upper and a lower part of the chamber 12$c$, wherein the diaphragm 15 can be implemented by a very thin foil to the body, which is On the one hand hermetically tight mounted to the housing of the implant On the other hand, plate stiffness, defines by the geometrical dimensions of the foil and the young modulus, should be so low that the intrinsic stress of the foil induced by the changes of the pressure to be measured does not influence the measurement signal significantly.

Alternatively, the diaphragm 15 can be firm/having a reduced flexibility.

The chamber 12$c1$ is covered by a thin foil, here a thin titanium foil 17$s1$, wherein the chamber 12$c2$ is covered by a comparable foil, e.g., the same foil 17$s2$. By use of these two foils 17$s1$ and 17$s2$, the chamber 12 is hermetically sealed against the surrounding.

In this embodiment, the housing 12 comprises another hermetically sealed portion for the control system 14. Here, the control system 14 is arranged within a hermetically tight titanium housing.

According to embodiments, the chamber 12 or especially the first part of the chamber 12$c1$ and the second part of the chamber 12$c2$ can be filled with an oil or a casting compound. This is marked by the reference numeral 13. The oil or casting compound has the purpose to apply the pressure applied to the foils 17$s1$ and 17$s2$ to the membrane of the pressure sensor 14. Here it should be noted that the pressure sensor 14 in the sensing chamber 12$c$ is embedded in this oil. Alternatively to the oil, an non-conductive, incompressible non-harmful liquid like the biocompatible oil 13 can be used. Regarding the liquid, it should be further noted that according to embodiments, it is possible to prime the chamber 12$c$ with the incompressible liquid, advantageously without bubbles. Bubbles can influence the measurement, as gas is compressible.

Here, the implant may be arranged within the human body, so that two different pressures of the body can be measured. For example, at the second pressure side 12$s2$ the body pressure P2 can be measured, while at the first pressure side 12$s1$, the reservoir pressure or cuff pressure P1 can be measured.

To summarize, this embodiment enables to measure by use of the differential pressure sensor 14, arranged within a pressure measurement chamber 12 to measure a pressure difference between an upper region 12$c1$ and a lower region 12$c2$ of the chamber 12$c$. The pressure sensor 14 is here mounted on the diaphragm 15, which separates the upper and the lower part 12$c1$ and 12$c2$ of the chamber 12$c$. The diaphragm 15 is according to further embodiments, rigid. It can be contained by electrical conductors to conduct the pressure sensor to the system control 16 and to read out the sensor 14. For the mounting of the pressure sensor 14 to the chamber 12*c* state of the art methods to mount pressure sensors with little stress can be applied.

Figure 3B:
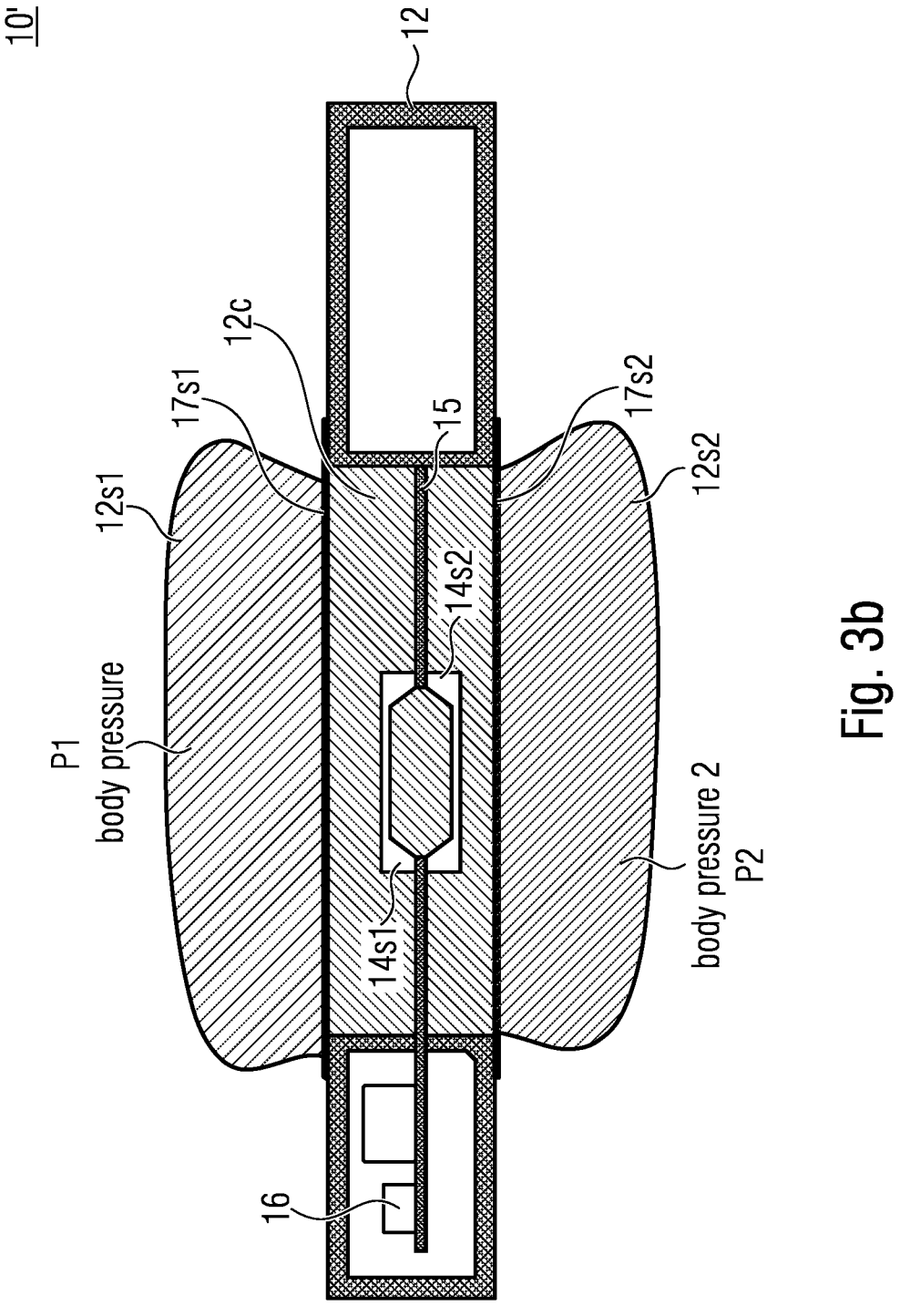

FIG. 3*b* shows an implant 10' which complies with the implant 10 with respect to the housing 12, the chamber 12*c*, the control unit 16 and the diaphragm 15. Furthermore, this implant 10' comprises the two foils 17*s*1 and 17*s*2 covering the chamber 12*c*. Within the chamber 12*c*, two pressure sensors 14*s*1 and 14*s*2 are arranged. These two pressure sensors 14*s*1 and 14*s*2 are arranged on two opposite sides of the diaphragm 15, so that the pressure sensor 14*s*1 is configured to determine the pressure P1 at the side 12*s*1, wherein the pressure sensor 14*s*2 is configured to determine the pressure P2 at the side 12*s*2. Expressed in other words, that means that two absolute pressure sensors 14*s*1 and 14*s*2 are mounted, such that one with contact that the upper chamber and the other in contact with the lower chamber. The differential pressure can be determined by calculating the difference between the two pressure values. This packaging can be simpler and easier when compared to the packaging of FIG. 3*a*, since no hole in the stiff separation chamber is needed.

Both embodiments of the implant 10 and 10' enable to fulfill the task of the hermetical sealing as well as the task of the differential pressure measurement. According to further embodiments, additional sensors, e.g., N sensors can be placed within the chamber 12*c*, both differential sensors or absolute sensors. For example, the plurality of N sensors can be fixed to the diaphragm 15.

Figure 4A:
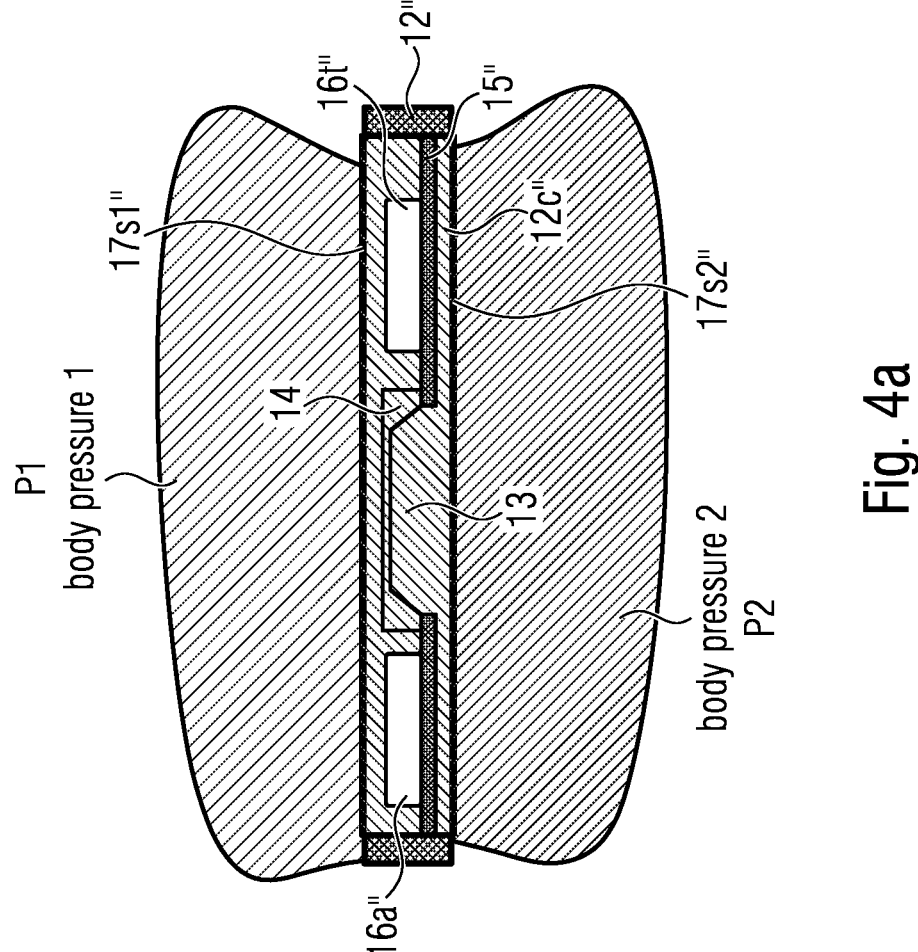
FIG. 4*a* shows another schematic implementation of an implant according to another embodiment.

In context of FIGS. 4*a* and 4*b*, another implant 10" will be discussed. FIG. 4*a* shows an implant 10" comprising a housing 12". Within the housing, an increased chamber 12*c*" can be formed. As discussed in context of FIGS. 3*a* and 3*b*, a diaphragm 15" may extend through the chamber 12*c*", substantially in parallel to the foils 17*s*1" and 17*s*2" encapsulating the chamber 12*c*". On the diaphragm 15", the sensor 14 as well as control elements 16*a*" and 16*t*" (e.g., ASIC and transponder) can be arranged. The two entities 16*a*" and 16*t*" can be arranged on the same side or on different sides with respect to the pressure sensor 14.

All three elements 16*a*", 14 and 16*t*" are arranged within the chamber 12*c*", which can be filled with liquid or oil. Here, the electronic 16*a*", 16*t*" and the sensor 14 is embedded in the oil 13. This arrangement enables to reduce the pressure differential measurement unit 10" with regard to its size. Here, the sensor can have a thickness of 1*mm* or smaller than 1 mm.

With respect to FIG. 4*b*, it will be discussed how to fix the pressure differential sensor/implant 10" to a human body. Here, the implant 10" should be attached to a body diaphragm 22. This diaphragm 22 separates two pressure zones P1 and P2. The housing 12", here a titanium housing can be attached to the body diaphragm 22 by use of biocompatible fixture material 23. Here, it might be helpful to combine the titanium sensor element 10" with the biocompatible material, wherein the titanium housing as well as the body diaphragm 22 can be fixed by surgeon.

Figure 5:
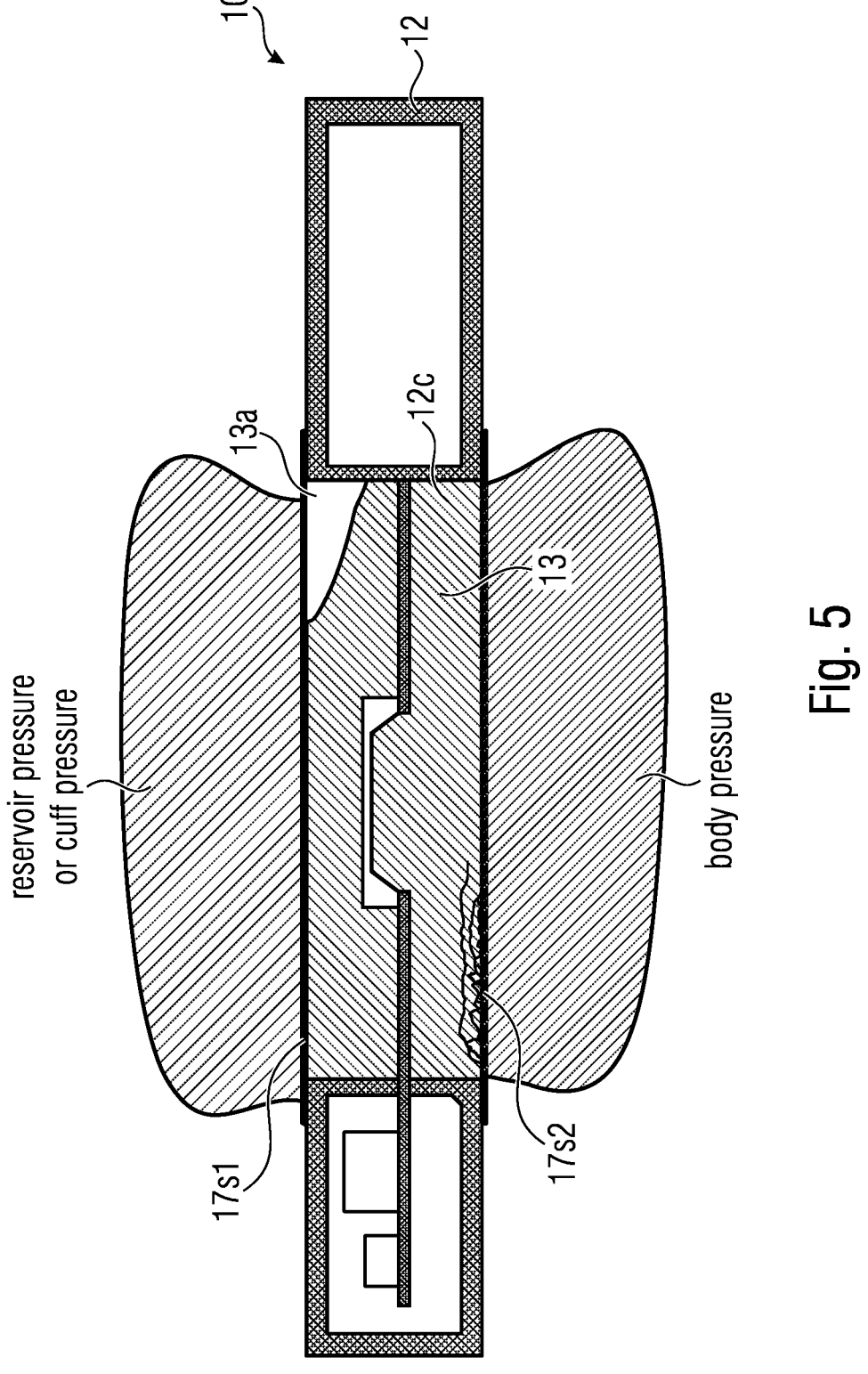
FIG. 5 schematically shows an enhanced variant of the implant of FIG. 3*a* according to further embodiments.

FIG. 5 shows the implant 10 comprising the housing 12. The chamber 12*c* is filled with oil. Here, two different priming methods are available. According to a first alternative, before mounting the second foil 17*s*2 hermetically to the housing 12 the priming can be performed. The advantage is, that there is no priming procedure or no priming ports necessary. However, it might be difficult to handle a liquid during the process parameter of the sealing process. According to another alternative, the priming may come after the mounting the foils 17*s*1 and 17*s*2 hermetically sealing the housing 12. Here the priming ports (not shown) are used to prime the chamber sections 12*c*1 and 12*c*2. The ports can be arranged as follows:

E.g. an inlet as well as an outlet both for the upper part and the lower part of the chamber, four priming ports are needed.

It might be easier to close these priming ports hermetically after priming compared to the foils.

Both chambers can have "guidance structures" to enhance a bubble free priming of the chambers. These structures could have the form of a meander, to avoid remaining bubbles in the edges of the chamber. The guidance structure should not disturb the pressure measurement function Alternatively to the oil, also a very weak casting but (compared to air) incompressible compound can be used instead of a liquid oil. That casting compound can be filled in the chamber during the mounting process of the pressure sensor diaphragm, and before the second titanium foil id hermetically mounted.

As illustrated by FIG. 5, within the chamber 12*c* the air bubble 13*a* may be caused during the priming. The influence of this gas bubble 13*a* in the sensor chamber 12*c* will be discussed below.

If there is an air (or gas) bubble in the sensor chamber (either in the top chamber or in the bottom chamber) with the volume $V_{gas}$ at atmosphere pressure $P_o$, the measurement accuracy will be affected.

Calculation: Fluidic capacitance of thin titanium foil: Cm $$C_m = \frac{dV_m}{dp}$$

For small deviations this fluidic capacitance can be calculated analytically from the theory of plates according to the geometry, the Young modulus and the Poisson ratio of the thin titanium foil.

The fluidic capacitance of a gas bubble (assuming atmosphere pressure $p_o$) can be approximated by isothermal equation of state:

$$C_{gas} = \frac{dV_{gas}}{dp} = \frac{V_{gas}}{p_0}$$

A pressure change of dp is changing the gas bubble volume $$dV_{gas} = C_{gas}dP$$

According to this volume change also the thin titanium foil can move:

$$dV_m = dV_{gas}$$

For the deflection of the thin titanium foil an intrinsic pressure dpi is needed:

$$dp_i = \frac{1}{C_p}dV_{gas} = \frac{1}{C_p}\frac{V_{gas}}{P_0}dp$$

This intrinsic pressure dpi will be the contribution of the gas bubble to the measurement error of the gas bubble.

According to embodiments, the chamber 12*c* may be filled by air instead of liquid. This has the advantage that no priming procedure is required, so as to enable an easier manufacturing process. However, The titanium diaphragms will move during the measurement according to the compressibility of the air. The intrinsic stress of the deflected titanium foils will influence the measurement.

If the absolute pressure is changing (e.g. patient in airplane), the fluidic capacitance of the trapped air bubbles is changing, and with it the correction factor of the pressure measurement Regarding the control electronic 16, it should be noted that according to embodiments, a temperature sensor can be integrated into the implant 10, to compensate temperature variations inside the body, e.g., by fever, etc.

Regarding the material, it should be noted that

In principle every material, which is qualified for long term implants can be used. For example, there is PEEK available for material for implants, however, a thin PEEK foil hardly can be made hermetically tight. Practically, titanium would be an advantageous solution both for the housing as well for the foil.

Regarding the foil, it should be noted that with a titanium foil with a thickness between 20 . . . 50 μm, and lateral dimensions (pressure measurement area) of the foil of 5 . . . 15 mm, this function should be ensured.

With respect to FIGS. 6*a* and 6*b*, an additional feature will be discussed.

Figure 4B:
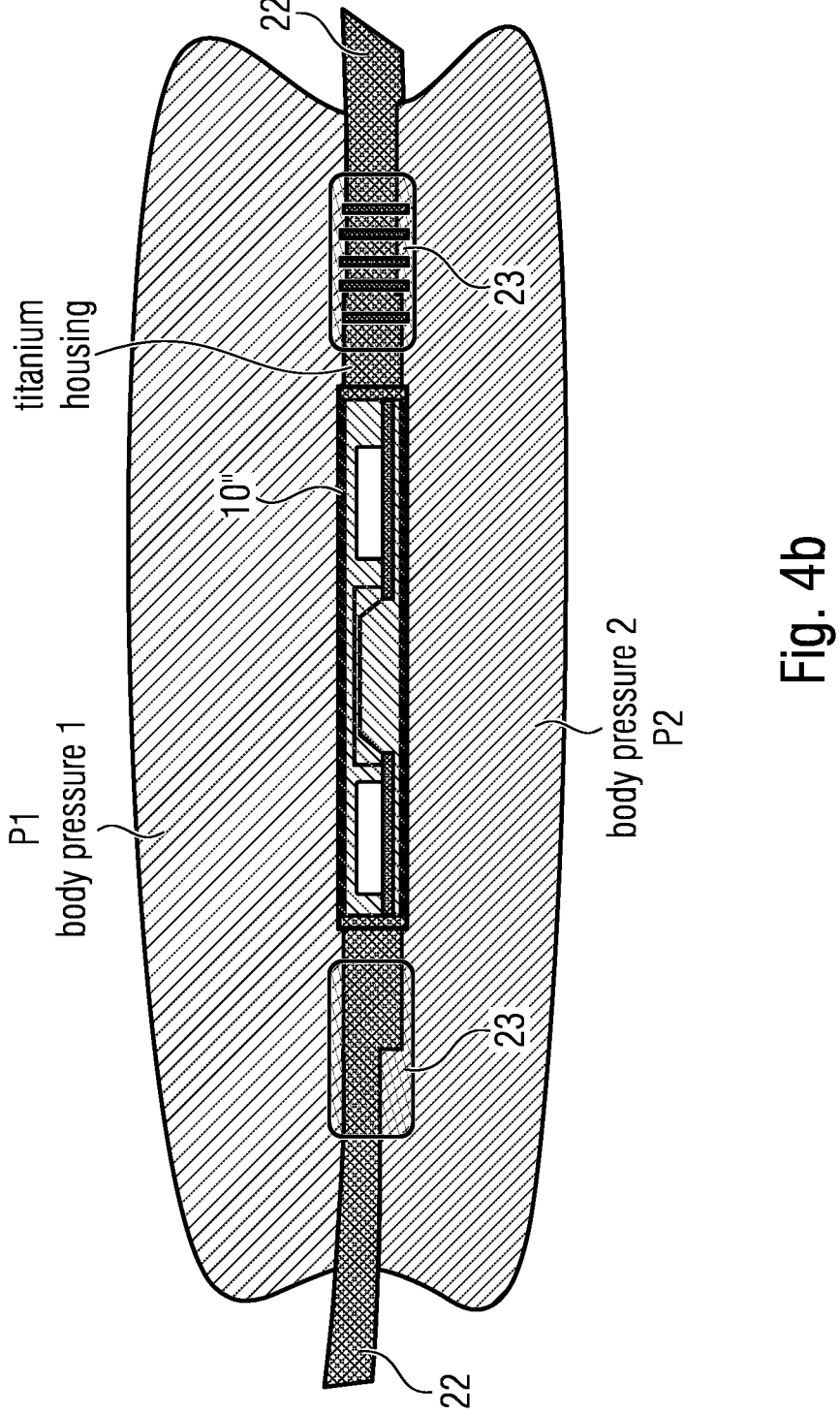
FIG. 4*b* shows the schematic implant of FIG. 4*a* implanted into a body according to another embodiment.
Figure 6A:
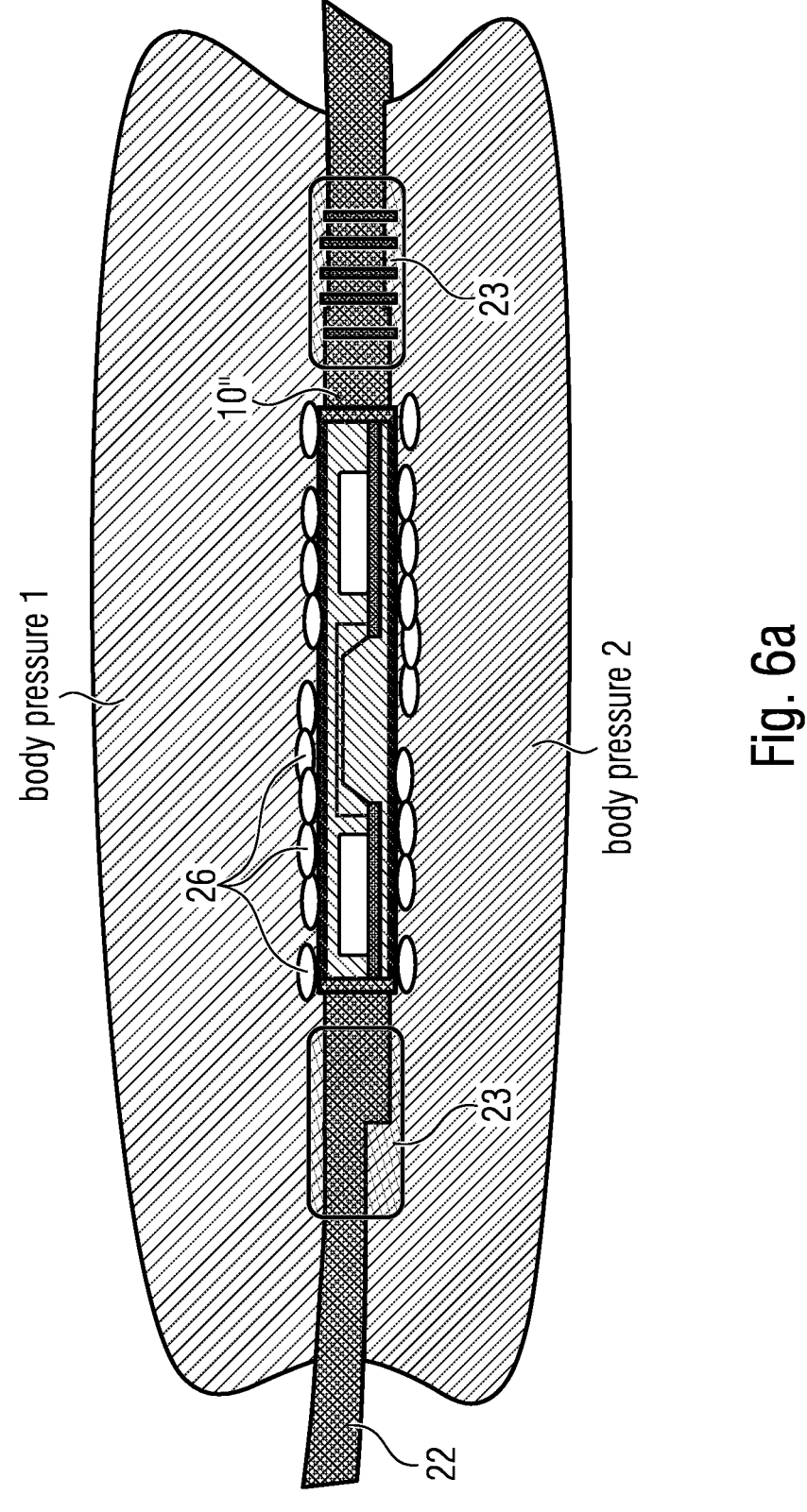
FIGS. 6*a* and 6*b* schematically show an enhanced variant of the implant according to FIG. 4*a* according to further embodiments.

FIG. 6*a* shows the implanted situation of FIG. 4*b*, where the implant 10" is attached to a body diaphragm 22 by use of biocompatible fixture material 23.

Figure 6B:
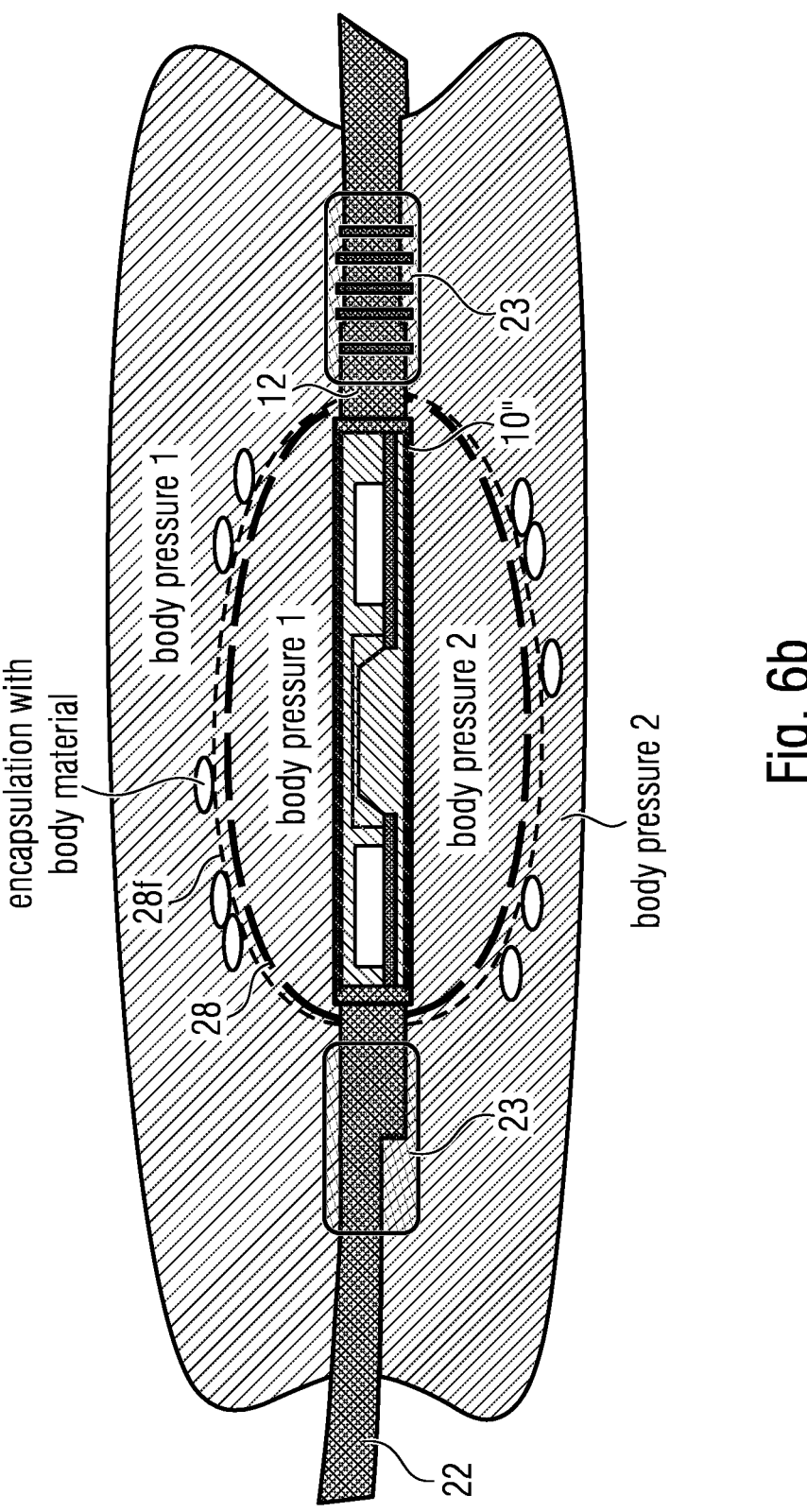

One probable measuring pressure or pressure difference in the body might be that after a certain time the pressure sensor is encapsulated by body material 26. This might generate two problems:

The layer of body material 26 is deposited at the pressure sensitive side 12*s*1, 12*s*2, generating a mechanical stress to the diaphragm, influencing the measurement result of the pressure sensor The layer could be a pressure barrier, with that a pressure drop can occur at that barrier A solution for this problem is illustrated by FIG. 6*b* showing the same arrangement as shown by FIG. 6*a*, wherein the implant 10" is enhanced by a filter bag 28*f*. This filter bag 28*f* can combined with a support 28 and has the task to separate the pressure sensitive titanium diaphragm 10" from the body 26. This filter bag 28*f* can be supported by a rigid grid 28 to avoid a mechanical impact, force or pressure to the measurement diaphragm. With that, only very small molecules (water, oxygen, CO2, glucose, etc.) or no cells or other molecules which might acclimate to a layer can pass that filter 28*f*. Note, alternatives for the grid 28 comprising a filter 28*f* or filter bag 28*f* are a conventional grid, rigid grid or in general porous element. The pores of the porous element, filter 28*f* or grid may be advantageously smaller than the cells or other body material, which can agglomerate and/or deposit to the pressure sensitive titanium diaphragm (e.g. smaller than 200 nm or smaller than 50 nm).

The filter area 28*f* is large enough that during the envisaged implant time the pressure sensor 16 will not be completely encapsulated in a way, that there is a significant pressure drop between body and the area above the titanium membrane.

Next, no material can pass the filter area to induce stress to the titanium membrane 10".

Note the differential pressure sensor and/or the implant 10, 10', 10" can comprise fixture to be connected to a human body membrane separating two different pressure sides/zones within the body. Another application is the usage in combination with cuff reservoir.

Here, the above described differential pressure measurement can be used for artificial implantable sphincter prosthesis for urethra (alternatively there are also applications for replacement of other body sphincter functions like anal sphincter, upper oesophageal sphincter, pyloric sphincter, ileocecal sphincter, . . . ) Prosthesis setup:

hydraulic actuated implant, that is able to close the urethra to get a patient into continent state, as well as open the urethra to allow the patient to urinate hydraulic actuation fluid is saline water, that is moved by mechanical or electrically driven pumps for closing or opening the urethra, a so called cuff, which is an inflatable longish balloon, is wrapped around the urethra in a circular form to replace the closing function of the previous human sphincter muscles a second inflatable reservoir, the so called balloon reservoir, is positioned within the abdomen of the patient, to store the pumped fluid, when the cuff is opened for urinating for system control and saving urethra tissue from getting pressed to strong, it is important to measure the urethra closing pressure compared to the ambient body pressure In this way the following pressures can be determined:

the abdominal body pressure can be measured by sensing the pressure within the balloon reservoir fluid line the urethra closing pressure can be measured within the cuff fluid line Thus, a differential pressure sensor between those two fluid lines within the implant can give those sensor values.

Optional specifications for that application:

hermeticity between fluid lines and sensor electronic fully differential pressure measurement between urethra-cuff-pressure and body-abdominal-pressure.

In this application, the implantable differential pressure sensor is embedded in an environment with saline solution, not body liquid. At both pressure sides there is no body liquid. Here, additional measures to protect the diaphragm (FIG. 6) are not needed.

Furthermore, this pressure sensor can be used also in applications measuring the pressure difference between reservoir of saline solution and body liquid.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a microprocessor, a programmable computer or an electronic circuit. In some embodiments, some one or more of the most important method steps may be executed by such an apparatus.

Some embodiments according to the invention comprise a data carrier having electronically readable control signals, which are capable of cooperating with a programmable computer system, such that one of the methods described herein is performed.

A further embodiment comprises a processing means, for example a computer, or a programmable logic device, configured to or adapted to perform one of the methods described herein.

A further embodiment comprises a computer having installed thereon the computer program for performing one of the methods described herein.

In some embodiments, a programmable logic device (for example a field programmable gate array) may be used to perform some or all of the functionalities of the methods described herein. In some embodiments, a field programmable gate array may cooperate with a microprocessor in order to perform one of the methods described herein. Generally, the methods are advantageously performed by any hardware apparatus.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. Implant comprising:
a housing with a chamber;
a sensor unit;
a first membrane covering the chamber at a first pressure side and a second membrane covering the chamber at a second pressure side;
wherein the chamber comprises a pressure transfer device being in contact to the first and second membranes and to the sensor unit arranged within the chamber between the first and second membranes; wherein a sensor control unit arranged within the housing;
wherein the sensor unit is configured to determine a pressure difference between a pressure at the first pressure side of the chamber and a pressure at the second pressure side of the chamber;
wherein the chamber extends from the first pressure side to the second pressure side through the housing and wherein the housing comprises a diaphragm separating the chamber in a first and a second parts; wherein the diaphragm holds the sensor unit;
wherein the first membrane comprises a first foil and wherein the second membrane comprises a second foil and wherein the chamber is covered by the first foil on the first pressure side and by the second foil on the second pressure side so as to hermetically seal the chamber; and
wherein the implant comprises a fixture configured to be connected to a body membrane separating the first and second pressure sides, wherein the sensor unit determines the pressure difference between the first and second pressure sides.

2. Implant according to claim 1, wherein the sensor unit comprises a sensor membrane configured to measure a relative pressure between a pressure applied from the first pressure side to a first side of the sensor membrane and a pressure applied from the second pressure side to a second side of the sensor membrane of the sensor unit.

3. Implant according to claim 1, wherein the sensor unit comprises a sensor arrangement with a first pressure sensor and a second pressure sensor, wherein the first pressure sensor is configured to measure the pressure at the first pressure side and wherein the second pressure sensor is configured to measure the pressure at the second pressure side.

4. Implant according to claim 1, wherein the housing comprises the diaphragm on which the sensor unit or the sensor control unit is attached; or
wherein the diaphragm extends through the chamber.

5. Implant according to claim 1, wherein the first foil on the first pressure side and the second foil on the second pressure side hermetically seals the chamber; or
wherein the housing hermetically seals the sensor control unit.

6. Implant according to claim 1, wherein the pressure of the first pressure side is applied via the first foil and the pressure transfer device to the pressure sensor and wherein the pressure at the second pressure side is applied via the second foil and the pressure transfer device to the pressure sensor; or
wherein the pressure at the first pressure side is applied to a first side of the pressure sensor via the first foil and the pressure transfer device and wherein the pressure at the second pressure side is applied to a second side of the pressure sensor via the second foil and the pressure transfer device.

7. The implant according to claim 1, wherein the first or second foil comprises a titan foil, a thin titan foil or a PEEK foil.

8. Implant according to claim 1, wherein the chamber or the first and second parts of the chamber are filled with an oil, a liquid or a casting compound forming the pressure transfer device; or
wherein the chamber or the first and second parts of the chamber are filled with an oil, a liquid or a casting compound forming the pressure transfer device and wherein the control unit is embedded within the oil, the liquid or the casting compound.

9. Implant according to claim 1, wherein the chamber or the first and second parts of the chamber comprises a guidance structures for guiding a liquid, oil or casting mold.

10. Implant according to claim 1, wherein the housing comprises a filter element out of a group comprising, a filter, a filter bag, a grid, a grid comprising a filter, a rigid grid or a porous element surrounding the chamber, the sensor unit or surrounding the first and the second foils of the housing.

11. Cuff reservoir comprising the implant according to claim 1, wherein the implant is part of the cuff reservoir, wherein the sensor unit determines the pressure difference between the pressure at the first pressure side and the pressure at the second pressure side within the cuff reservoir or of the cuff reservoir against a surrounding.

12. Method for producing the implant according to claim 1, wherein the method comprises arranging the sensor unit within the chamber or between two foils.

13. The method according to claim 12, wherein the method comprises priming the chamber or an area between the two foils; and
wherein priming is performed before or after attaching the first and the second foils to the housing.

* * * * *